(12) United States Patent
Bosse et al.

(10) Patent No.: US 7,648,486 B2
(45) Date of Patent: Jan. 19, 2010

(54) CANNULA PROTECTING COVER

(75) Inventors: Rainer Bosse, Kirchberg (CH); Stefan Jost, Bolligen (CH); Markus Ramseyer, Uetendorf (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 12/104,601

(22) Filed: Apr. 17, 2008

(65) Prior Publication Data

US 2008/0255526 A1    Oct. 16, 2008

Related U.S. Application Data

(63) Continuation of application No. 10/668,034, filed on Sep. 22, 2003, now Pat. No. 7,361,166, which is a continuation of application No. PCT/CH01/00173, filed on Mar. 20, 2001.

(51) Int. Cl.
*A61M 5/32* (2006.01)
(52) U.S. Cl. .................................................... 604/192
(58) Field of Classification Search ............... 604/931, 604/192, 198, 263, 48, 19, 110, 111
See application file for complete search history.

(56) References Cited

U.S. PATENT DOCUMENTS

| | | | |
|---|---|---|---|
| 5,322,517 A | | 6/1994 | Sircom et al. |
| 5,336,199 A | | 8/1994 | Castillo et al. |
| 5,342,320 A | * | 8/1994 | Cameron ..................... 604/192 |
| 5,374,255 A | * | 12/1994 | Nathan et al. ............... 604/192 |
| 5,492,536 A | * | 2/1996 | Mascia ........................ 604/197 |
| 5,591,138 A | | 1/1997 | Vaillancourt |
| 5,591,318 A | | 1/1997 | Li et al. |
| 5,681,291 A | | 10/1997 | Galli |
| 5,984,899 A | | 11/1999 | D'Alessio et al. |
| 6,217,559 B1 | | 4/2001 | Foster |
| 6,413,243 B1 | | 7/2002 | Geist |

FOREIGN PATENT DOCUMENTS

| | | |
|---|---|---|
| DE | 200 22 146 U1 | 8/2001 |
| EP | 0 413 872 A1 | 2/1991 |
| EP | 0 645 159 A1 | 3/1995 |
| GB | 2202747 A | 10/1988 |

\* cited by examiner

*Primary Examiner*—Nichola D Lucchesi
*Assistant Examiner*—Christopher D Koharski
(74) *Attorney, Agent, or Firm*—Dorsey & Whitney LLP; David E. Bruhn, Esq.

(57) ABSTRACT

A cannula cover for use with an injector or injection device, wherein the injector or injection device includes a dosing section and a cannula support, and wherein the cover is attached to the cannula support and can be retracted against a bias in order to expose a cannula, said cannula cover including, in one embodiment, a substantially closed front facing side having an openable cannula passage opening.

16 Claims, 15 Drawing Sheets

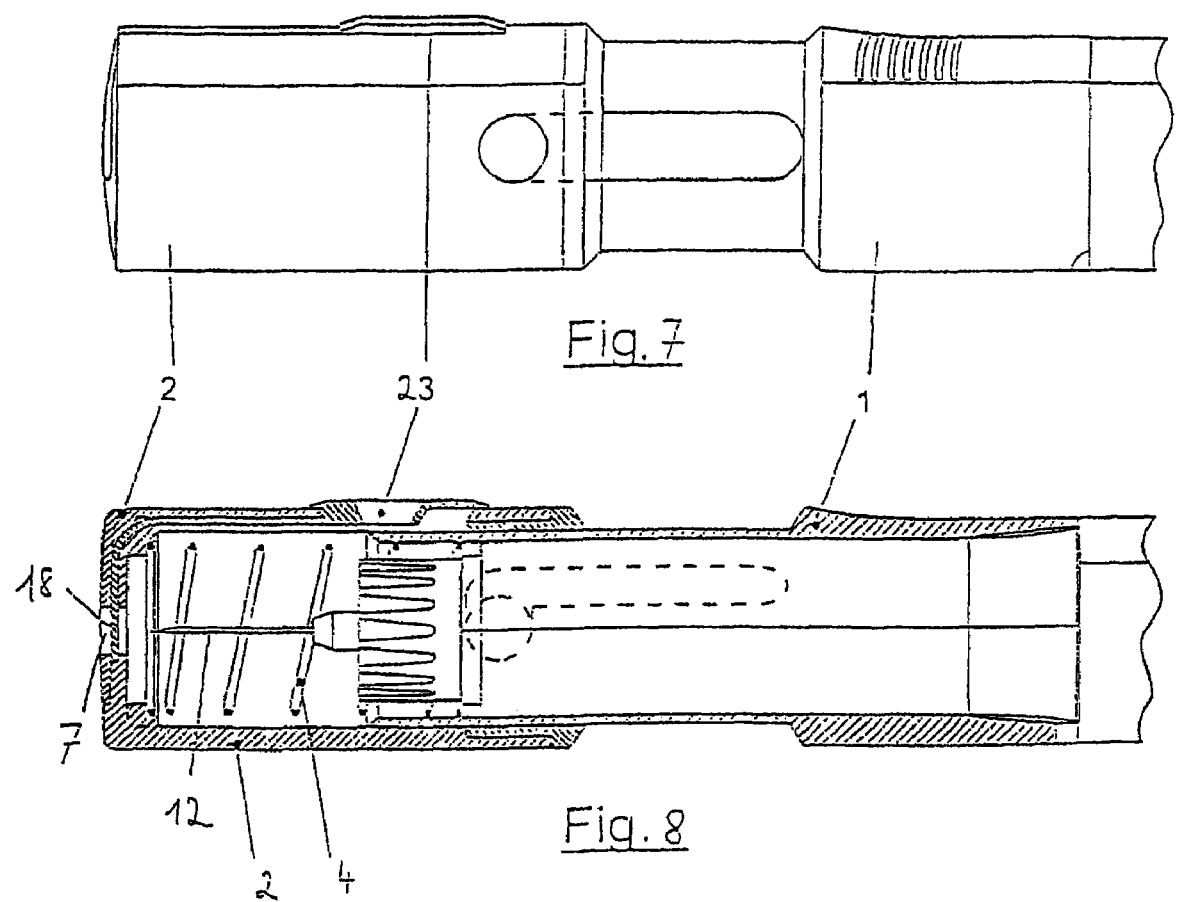

CANNULA PROTECTING COVER

CROSS REFERENCE TO RELATED APPLICATIONS

This application is a continuation of U.S. application Ser. No. 10/668,034 filed on Sep. 22, 2003, issued as U.S. Pat. No. 7,361,166, which is a continuation of International Application No. PCT/CH01/00173, filed on Mar. 20, 2001, the contents of which are incorporated herein by reference.

BACKGROUND

The present invention relates to a cannula protecting cover for an injector comprising a dosing section and a cannula support. Such injectors, also known in this technical field as "pens," serve to administer medicines under the skin by injecting and enable precise dosing and easy handling when used repeatedly.

Known, frequently used pens use a dosing section in which the medicine dosage to be administered is accommodated and which comprises an operating means, for example a button, for triggering the injection. For each administering, a new cannula is attached to the dosing section, by means of a generally screw-on cannula support. In a simple version, a loose protective cap is then attached via the cannula, in order to protect the cannula from contamination or damage. The disadvantage of this simple embodiment is that such a cap, as an individual piece, can be very easily lost. Furthermore, it is disadvantageously possible that the cap can no longer be correctly fixed on the dosing section once it has been used repeatedly and can unexpectedly come loose from the dosing section. The then exposed cannula presents a danger of injury and infection.

An automatically latching needle protecting cap is known from U.S. Pat. No. 5,609,577. This cap comprises a front portion which is provided circumferentially around the needle and has an open front facing wall. Once the front section has been rotated, it is unlatched and can be retracted against the bias of a spring in order to expose the cannula, as is necessary for administering the injection.

The disadvantage of this generic needle cover is again that the needle is still relatively unprotected in the initial state, since it is only protected from the sides by the front section. It is consequently still relatively greatly exposed to contamination and can in principle also still suffer mechanical damage.

SUMMARY

It is an object of the present invention to provide a cannula protecting cover which overcomes problems unaddressed or incompletely addressed by the prior art. In particular, the intention is to protect the cannula from contamination and mechanical influences, wherein simple handling of an injector or injection device fitted with the cannula cover is also possible.

This object is solved in accordance with the invention by providing the cannula cover with a substantially closed front facing side comprising a cannula passage opening. In general, the invention relates to a cannula cover for an injector, in some embodiments preferably comprising a dosing section and a cannula support, wherein the cover is attached to the cannula support and can be retracted against a bias in order to expose a cannula, said cannula cover comprising a substantially closed front facing side having a cannula passage opening.

One fundamental advantage is that the cannula is almost completely shielded against outside influences, i.e., against contamination or mechanical influences. The cannula thus remains largely sterile while installed, even over long periods of time, and cannot be inadvertently kinked or undesirably injected. The cannula cover is attached to the cannula support and can thus neither be lost nor sufficiently loosened in its attachment to present a danger of injury.

In a preferred embodiment, the cannula cover comprises a latch which may be unlatched by rotating the cover and prevents the cover from being retracted. This can ensure that the cannula is only exposed for proper use.

In accordance with one advantageous embodiment of the present invention, the cannula cover comprises a seal for the cannula passage opening. Such a seal for the cannula passage opening provides fully circumferential protection of the cannula and therefore protection during transport and against contamination.

In such an embodiment, the seal is formed such that it exposes the cannula passage opening when the cover is retracted via a movement-coupled exposing mechanism. In one embodiment, the seal may comprise two tongues with sealing sections at their front ends. These sealing sections close the cannula passage opening when the cover is advanced and are forced apart when the cover is retracted so as to expose the cannula passage opening.

In one embodiment, the tongues can be fixed at the rear base end of the cover, such that they are forced apart by a lever action at the front portion of the cannula support when the cover is retracted.

In accordance with an alternative embodiment of the cannula cover in accordance with the invention, the seal comprises a covering flap which is slid away from the cannula passage opening via a slaving means when the cover is unlatched by rotating it. In this embodiment, as in other embodiments, the principle is that the cannula passage opening is opened in a process or step which is part of the process performed to administer an injection. Once the covering flap has been slid away, the cannula can easily emerge through the cannula passage opening.

In another alternative embodiment, the seal comprises a sealing strip which may be shifted in a longitudinal guide in the cover and the front end of which can be slid away from the cannula passage opening by means of a slider on the cover. This provides a separate way of opening for the seal and prevents the seal from being inadvertently opened. In this embodiment, it can be possible to shift the sealing strip directly by longitudinally shifting the slider or by shifting the slider in the circumferential direction on the cover. In the latter case, a movement redirection via features or structures known in the art also has to be provided. In addition, when the slider is shifted in the circumferential direction on the cover, this operation can also simultaneously be used to unlatch the cover.

In some preferred embodiments, the cannula cover can be formed such that the cap can only be inserted when a pressure force directed towards the distal end is applied from the front, i.e., from the proximal end, such that retracting the cover by means of an operating element attached to the injector is not necessary or even not possible. This can ensure that the cover can only be moved so as to expose the cannula, when the front end of the injector is placed on an injection area and a force is then exerted on the injector by the user. This can prevent the cannula from being unintentionally exposed. The cannula cover can, of course, also be formed such that a user can move the cannula cover using a suitable operating element.

In one embodiment, the cover or cap is preferably arranged such that it can be shifted axially, i.e., in the longitudinal direction of the injector, wherein, however the cap is mounted for axial movement, it is secured against rotating, i.e., it cannot perform a rotational movement relative to the injector. A threaded insert may be coupled to the cap, said insert advantageously abutting the cap and converting an axial movement of the cap into an auto-rotational movement via a thread engaging with the injector, such that the threaded insert rotates relative to the cap when the cap is inserted into the injector. A spring element is advantageously provided which biases the threaded insert and/or the cap outwards, i.e., in the proximal direction, thus pressing the threaded insert against the cap.

In some embodiments, a latching mechanism is advantageously provided which can be unlatched by the user using a suitable operating element and which secures the cap against being unintentionally inserted into the injector.

In one preferred embodiment, a sealing element is provided which, in its resting state, seals the cannula passage opening of the cannula cover or cap and exposes said cannula passage opening when the cap is inserted, wherein, in particular, the rotational movement of the threaded insert relative to the cannula cover can be converted into an exposing movement of the sealing element.

BRIEF DESCRIPTION OF THE DRAWINGS

FIG. 7 is a lateral view of a third embodiment of a cannula cover in accordance with the invention;

FIG. 8 is a cross-section through the cannula cover in FIG. 7;

FIG. 9 is an exploded view of a fourth embodiment of a cannula cover in accordance with the invention;

FIG. 14, including

DETAILED DESCRIPTION

Figure 1:
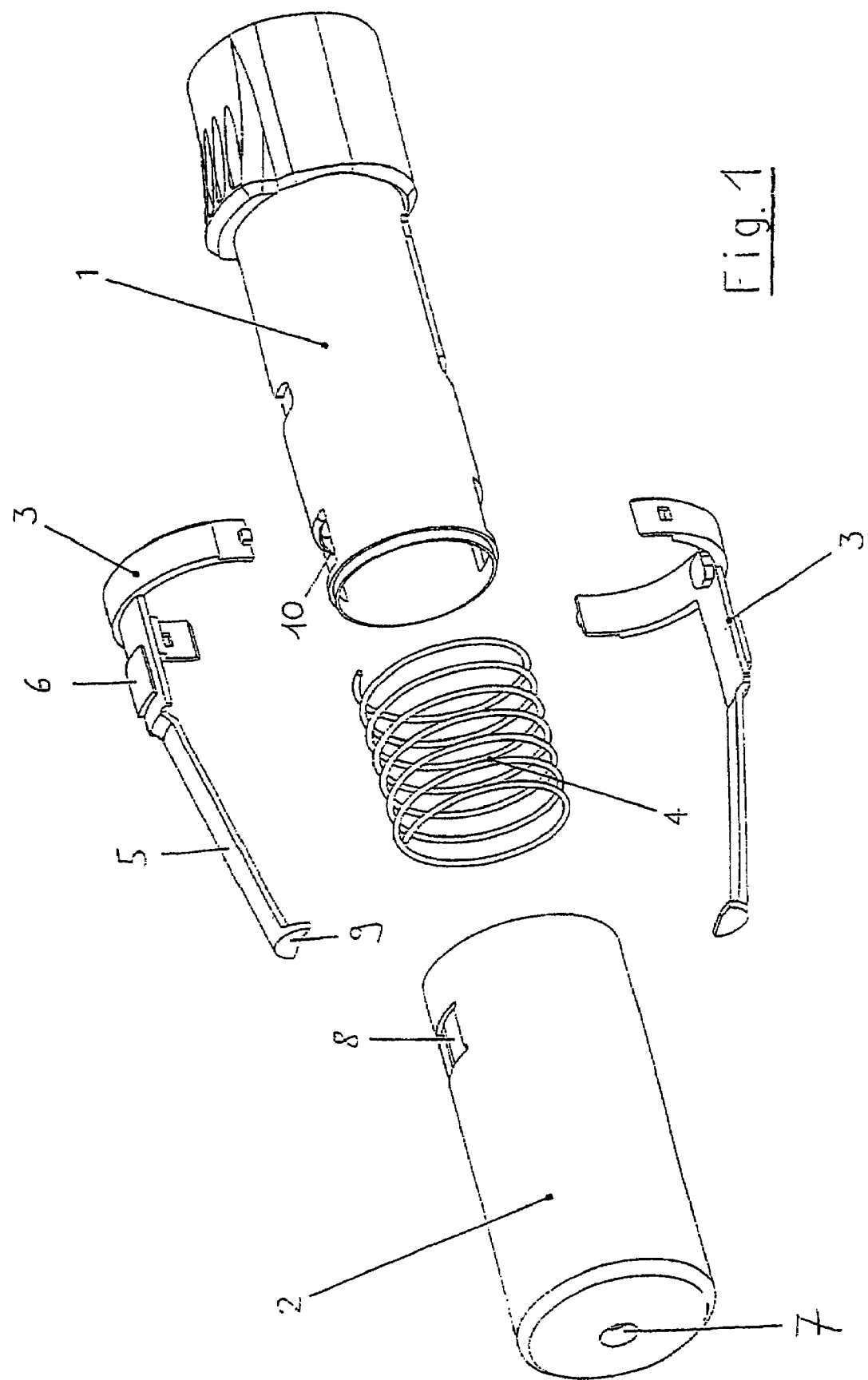
FIG. 1 is an exploded view of a cannula cover in accordance with a first embodiment of the invention.
Figure 2:
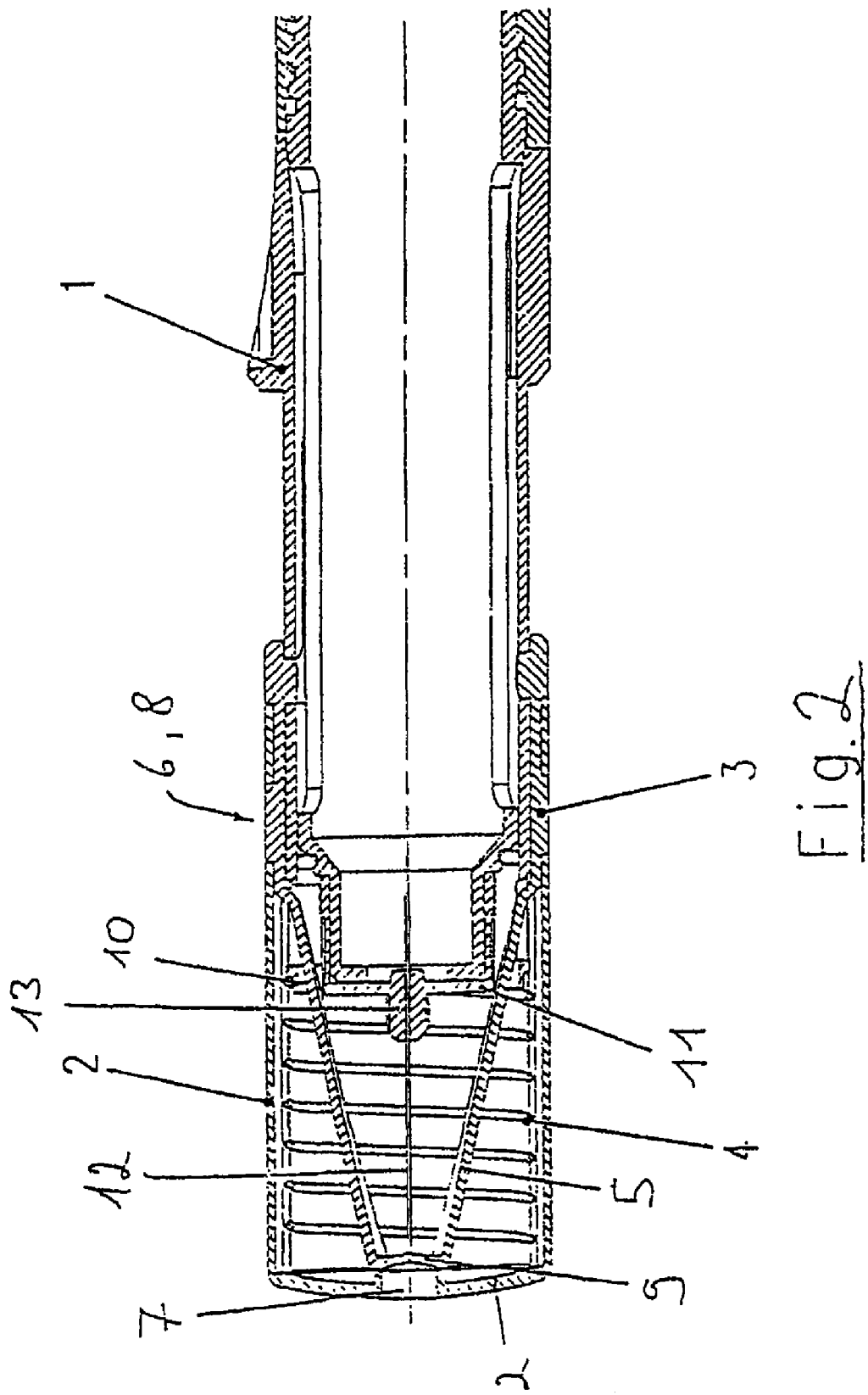
FIG. 2 is a longitudinal section through the cannula cover in accordance with FIG. 1.

A first embodiment of a cannula cover in accordance with the invention will be described in the following by referring to FIGS. 1 and 2. In FIGS. 1 and 2, and all the accompanying figures, identical reference numerals refer to identical or functionally identical components.

The cannula cover in accordance with a first embodiment of the present invention, as shown in FIGS. 1 and 2, comprises the attachment component 1 which is plugged onto the dosing section of an injector, i.e., for example, onto a so-called injection pen. The attachment component 1 has through holes 10 in its front section, the function of which will be explained below. The spring 4 is placed on the attachment component 1 at the front on suitable structure such as a circumferential facing shoulder (not indicated). Two sealing elements 3 are shown above and below the spring 4, said elements each comprising a half-ring at their base end, via which they can be stuck together. Furthermore, the sealing components each have a tongue 5, at the front end of which sealing sections 9 project inwards at right angles. In addition, the tongues 5 also comprise locking attachments 6 in their base area.

FIG. 1 furthermore shows the front cap 2 which is substantially closed at its front end, except for the central cannula passage opening 7. In addition, it comprises passages 8 which the attachments 6 can lock into.

In the assembled state, the cannula opening in accordance with FIG. 1 is shown in FIG. 2. The front edge 11 of the cannula support, the cannula 12 and the cannula support 13 are also shown in FIG. 2 as additional components. Thus assembled, the two sealing components 3 are connected to each other via their half-rings. The tongues 5 of the sealing components 3 are guided through the openings 10 into the interior of the spring 4, and when the cap 2 is then placed on top, the two sealing sections 9 come together inside in front of the cannula passage opening 7 and seal it. The cannula in the initial state shown in FIG. 2 is thus completely protected against contamination and external mechanical influences.

Despite this all-round protection, however, the injector is ready for use at any time. If the cap 2 is shifted back (to the right in the figure) against the force of the spring 4, the two tongues 5 are pushed apart by the front sections 11 of the cannula support 13, the sealing sections 9 move away from each other, and the cannula 12 can easily emerge through the cannula passage opening 7. The injection can then be administered, and the cap 2 is then pushed back into the position in FIG. 2 by the spring force of the spring 4, such that the cannula is again completely shielded outwards and cannot injure or infect anyone or be damaged.

Figure 3:
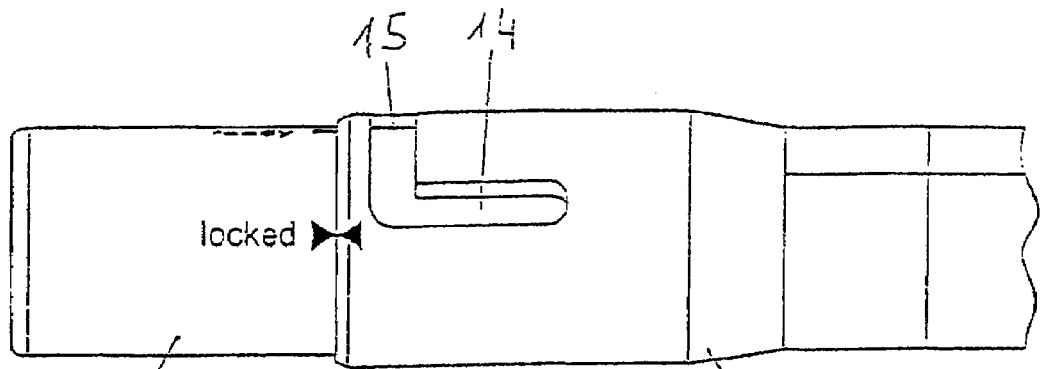
FIG. 3 is an exterior view of a second embodiment of a cannula cover in accordance with the invention.
Figure 4:
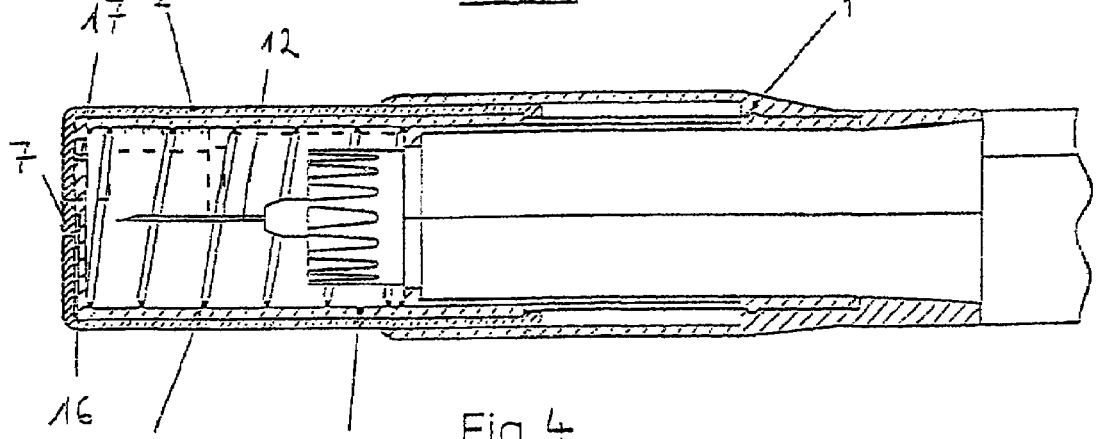
FIG. 4 is a longitudinal section through the cannula cover in accordance with FIG. 3.
Figure 5:
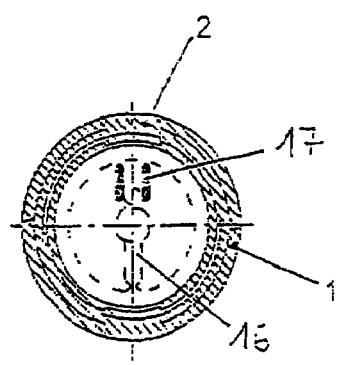
FIG. 5 is a cross-sectional views of the cannula cover in accordance with FIGS. 3 and 4, sealed and opened, respectively.

Another embodiment of a cannula cover in accordance with the invention is shown in FIGS. 3 to 6. A lateral exterior view of said cannula cover in accordance with this embodiment is shown in FIG. 3, and the cap 2 and the attachment component 1 may be seen in this view. The cap 2 is here formed such that it has a smaller outer diameter than the front end of the attachment component 1 and can be shifted in the attachment component 1. The ability to shift is controlled by a latch which consists of the guiding groove 14 in the front portion of the attachment component 1, formed at right angles, and a latching attachment 15. As shown, the cap 2 is latched and cannot be shifted to the right. If the cap 2 is then rotated such that the attachment 15 moves in the circumferentially arranged section of the guide 14 as far as the corner, the cap 2 is unlatched and can be retracted to the right, wherein the attachment 15 moves in the axial portion of the guiding groove 14.

The above movement expels the cannula 12 (FIG. 4) through the cannula passage opening 7, once a latching mechanism has been opened, as will now be described. The latching mechanism consists of a covering flap 16 and a slaving means 17 which comprises two stays running in parallel. These components may be seen in their arrangement in FIGS. 4 to 6. The slaving means 17 grips around an upper end of the covering flap 16, which when latched lies in front the cannula passage opening 7 via its central, expanded or swelled portion. On the opposite side, the covering flap 16 is mounted, such that it can rotate, via a film joint.

Figure 6:
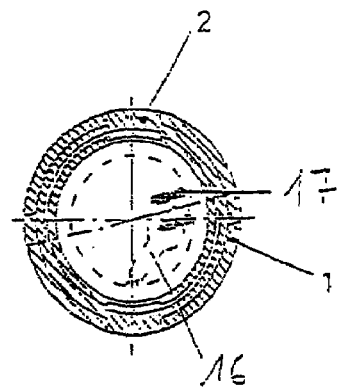
FIG. 6 is a cross-sectional views of the cannula cover in accordance with FIGS. 3 and 4, sealed and opened, respectively.
Figure 3:
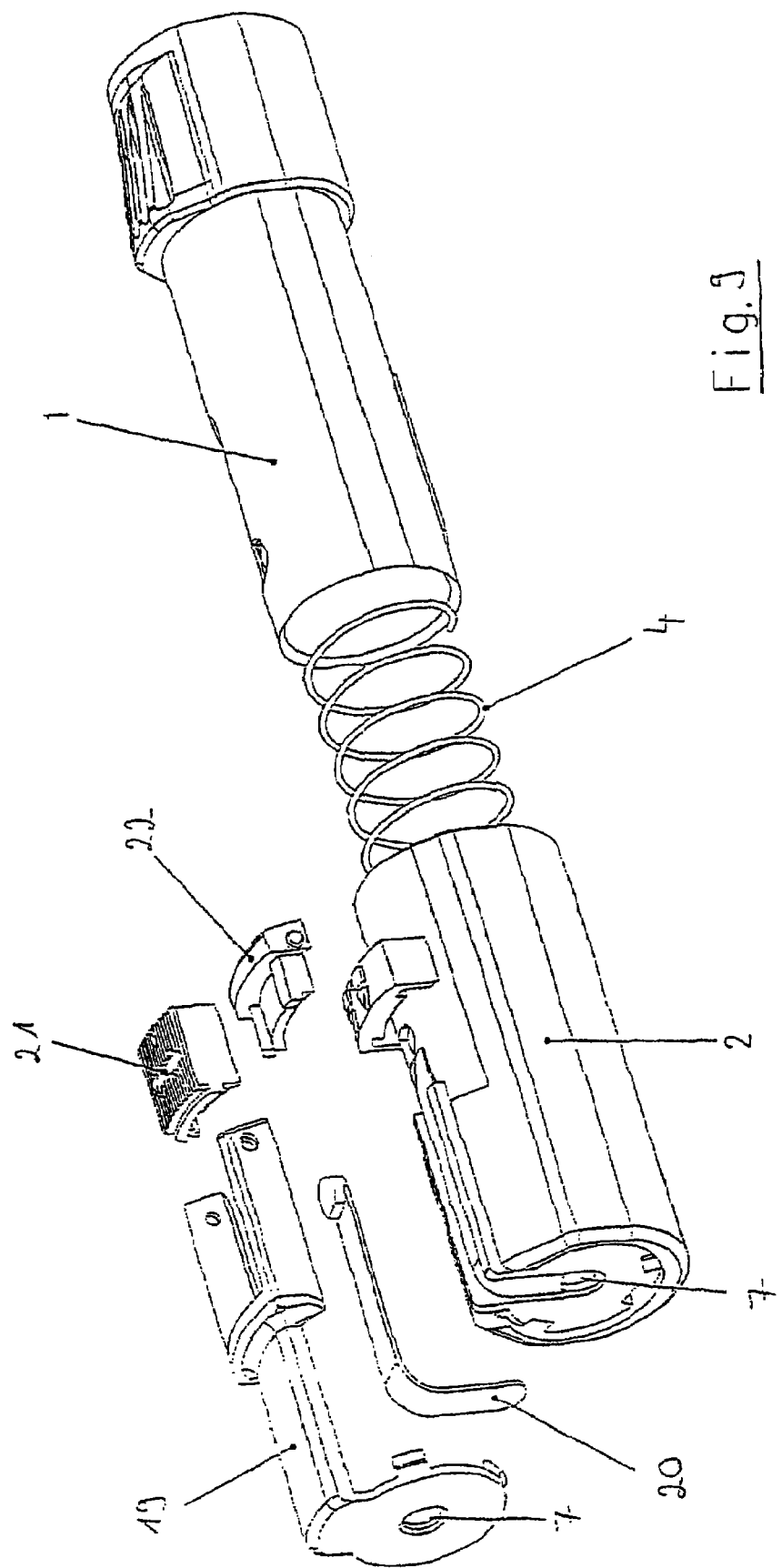

If the unlatching movement described above is then performed, the slaving means 17 moves together with the cap 2 and slides the covering flap 16 away from the cannula passage opening 7 in a rotational movement. This state is shown in FIG. 6. Once the cannula passage opening 7 has then been exposed, the cap 2 can be shifted backwards (to the right) against the force of the spring 4, and the cannula 12 can emerge forwards through the passage opening 7. Once the injection has been administered and the cap restored by means of the spring 4, the cap is latched again by a reverse rotation, and the covering flap 16 is again situated in front of the cannula passage opening 7.

A third embodiment of the present invention is shown in FIGS. 7 and 8. In this embodiment of the cannula cover, the cap 2 again sides over the front portion of the attachment component 1, as in the first embodiment. A latching guide is also provided which functions in a way similar to that of the second embodiment. The third embodiment shown in FIGS. 7 and 8 differs specifically from the two previously described embodiments in its seal for the cannula passage opening 7.

As shown from the exterior in FIG. 7 and in section in FIG. 8, the cap comprises a slider or switch 23 which is separately provided for opening the cannula passage opening 7. A latching strip 18, extending forward at an angle toward the facing side is attached to the slider 23. As shown, this latching strip 18 extends in the cap in its longitudinal guide far enough to seal the cannula passage opening 7. If an injection is to be administered via the cannula 12, the slider 23 is shifted backwards on the cap 2 by hand, which retracts the front section of the latching strip 18 from the cannula passage opening 7. The latching mechanism can then be released by rotating the cap 2 and the cap 2 shifted backwards against the force of the spring 4 for an injection. Conversely, once the injection has been administered, the cannula passage opening 7 can be sealed again by sliding the slider 23 forward, wherein the latching strip 18 is restored to the position shown in FIG. 8.

Figure 10:
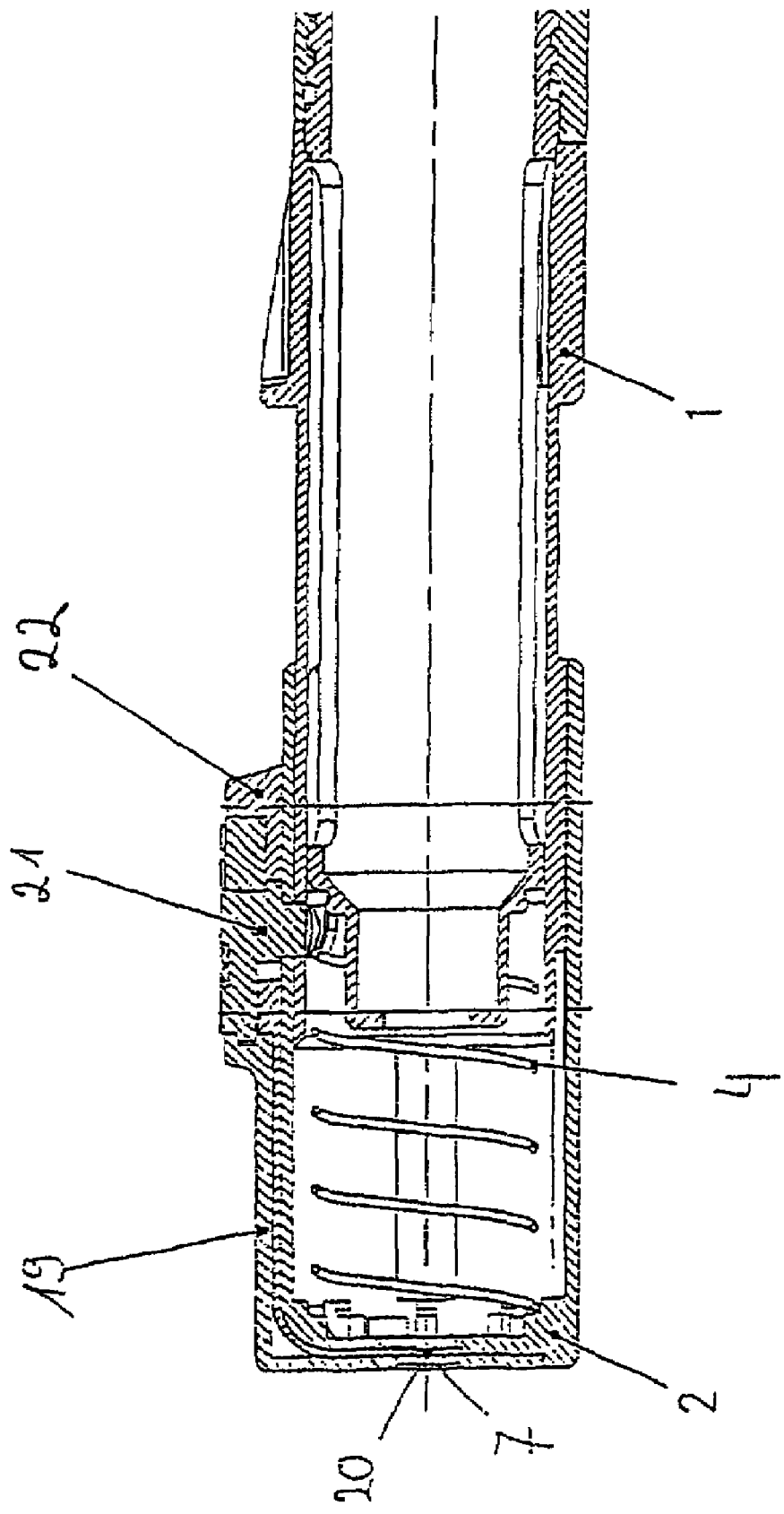
FIG. 10 is a longitudinal section through the cannula cover in accordance with FIG. 9.

A fourth embodiment of the present invention will be explained in conjunction with FIGS. 9 and 10. FIG. 9 shows an exploded view of the cannula cover in accordance with said fourth embodiment, while FIG. 10 shows a longitudinal section. In this embodiment, a number of elements are joined to the cap 2, namely the latching strip 20 for the cannula passage opening 7, the attachment 19 arranged over the latching strip, and the slider 21 including the rear slider element 22.

The fourth embodiment as set forth in FIGS. 9 and 10 operates generally and similarly to the third embodiment, using a latching strip 20 which in its initial state hides the cannula passage opening 7 with its front end. As opposed to the third embodiment, however, the latching strip 20 depicted in FIGS. 9-10 can be moved away from the cannula passage opening 7 by means of the slider 21 by moving it laterally in the circumferential direction, wherein it is guided between the attachment 19 and its guide in the cap 2. The movement of the slider 21 in the circumferential direction is redirected such that it generates a longitudinal movement of the latching strip 20 and/or unlatches the sealing cap.

Figure 11:
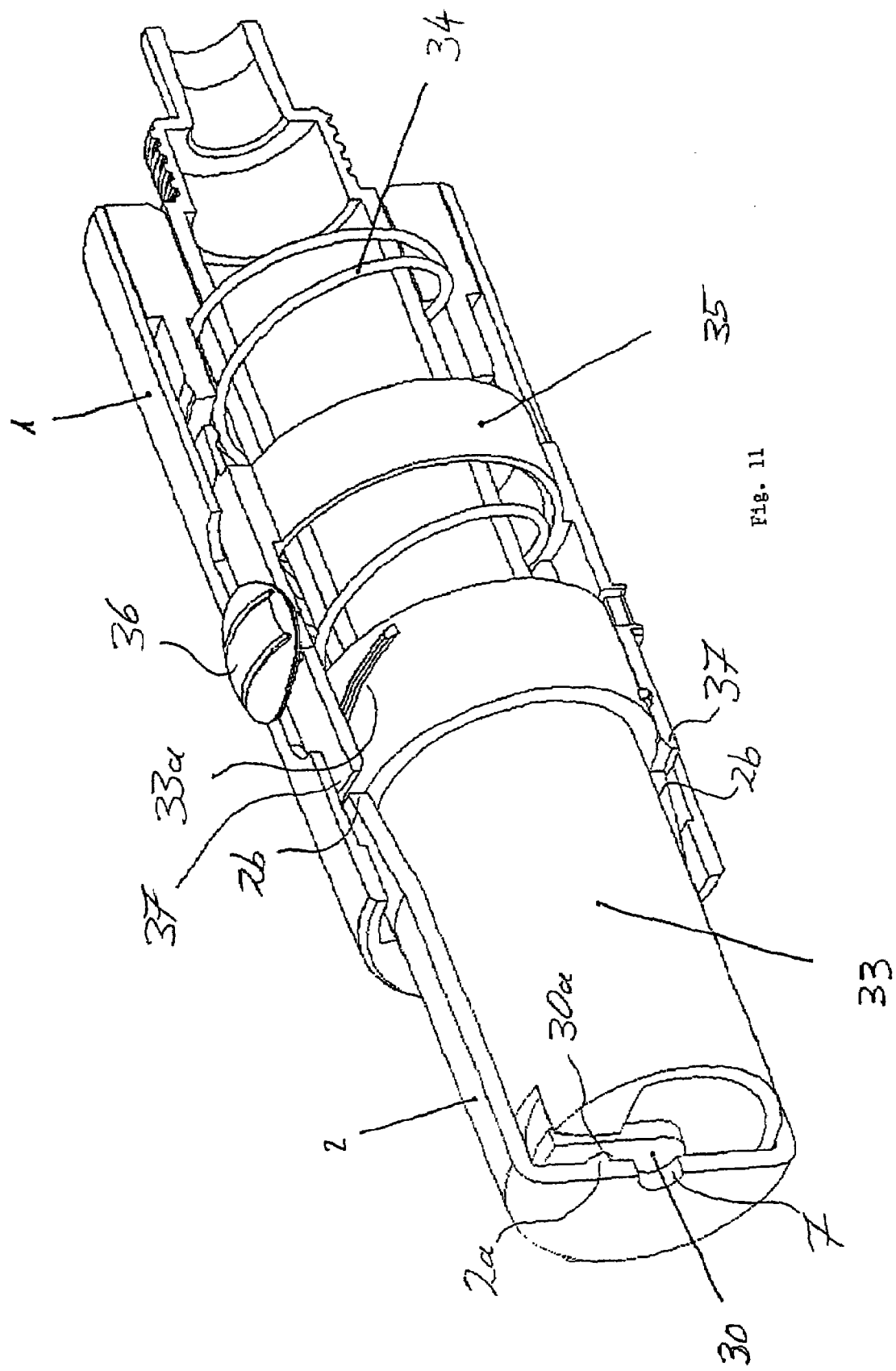
FIG. 11 is a perspective view, in a partial section, of fifth embodiment of a cannula cover in accordance with the invention, with the cannula passage opening closed.

A fifth embodiment of the present invention will now be explained with reference to FIGS. 11 to 14. FIG. 11 shows the cap 2 which is mounted, secured against rotating with respect to the injector, in particular with respect to the attachment component 1, for example by axially running guiding grooves. In this embodiment, the cap 2 thus can only move in the axial direction of the injector. A threaded insert 33 is provided within the cap 2, abutting the cap 2, wherein said insert engages with the attachment component 1 via a thread 33a and is biased outwards by the spring 34, thus pressing against the cap 2. The locking seal 35, which can be shifted outwardly (in FIG. 1, to the left) via the sliding element 36, comprises an element 37, chamfered on its underside, at its front end. The projection 2b of the cap 2 can be pressed downwards by said element 37 when said element is shifted outwardly, so as to be able to release the latch of the cap 2 via the projection 2b which protrudes outwardly and is supported against a holding element, and insert the cap 2 into the injector or attachment component 1. On an element 2a protruding inwardly from the cap 2, a sealing element 30 is mounted by a bore or recess 30a provided in the sealing element 30, such that the sealing element 30 can rotate about the element 2a. In FIG. 11, the cap 2 is in an exterior position and the sealing element 30 seals the cannula passage opening 7.

Figure 12:
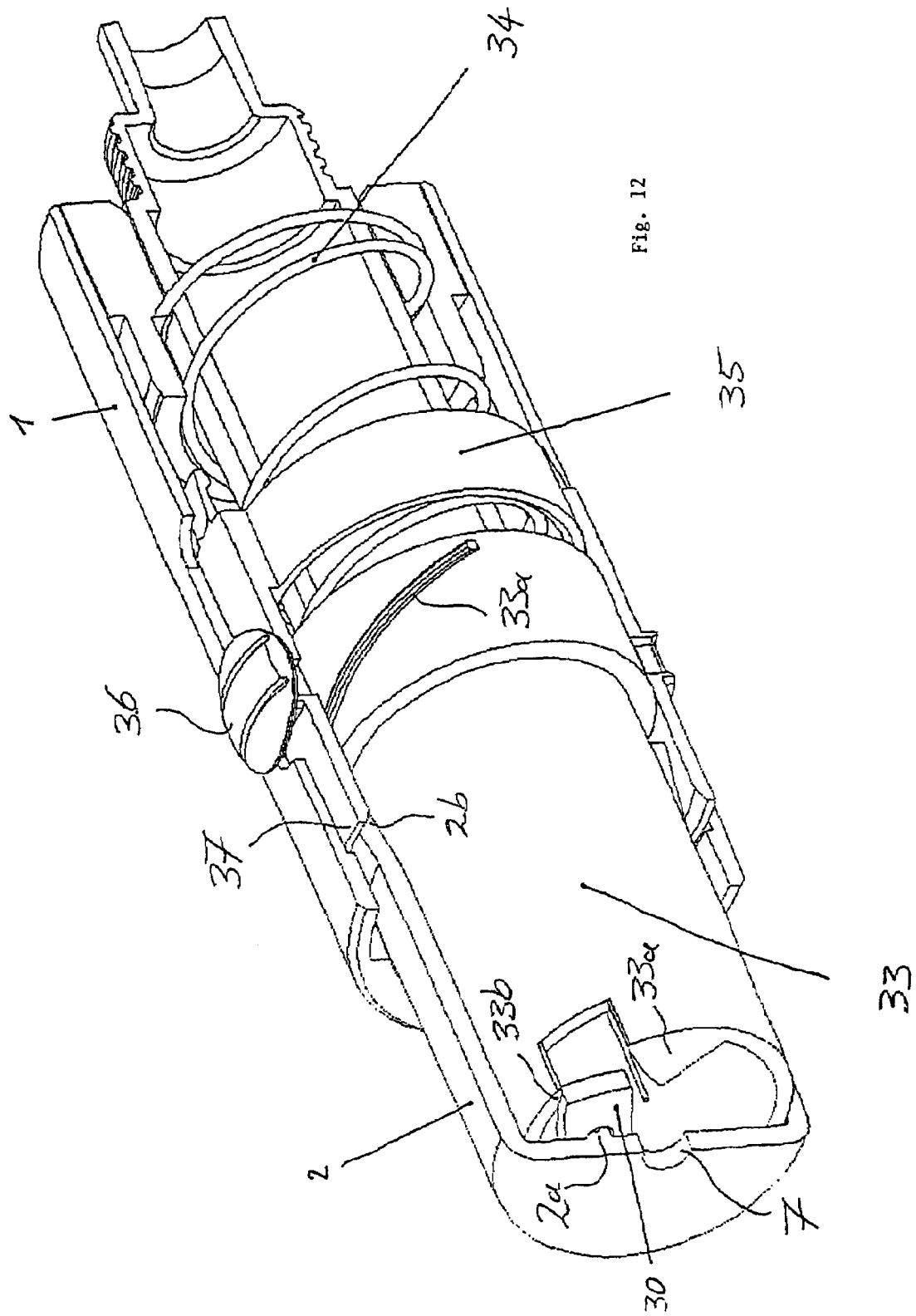
FIG. 12 depicts the cannula cover of FIG. 11, with the cannula passage opening open.

FIG. 12 shows the cap 2 unlatched, wherein the sliding element 36 is slid forward in order to push the locking projection 2b downwardly via the chamfered surface 37 and so enable an insertion movement of the cap 2 into the attachment component 1. Since the cap 2 is mounted, secured against rotating with respect to the attachment component 1, the cap 2 can only perform an axial movement relative to the attachment component 1 when pressure is applied from the front, wherein due to said axial insertion movement of the cap 2, the threaded insert 33 abutting the cap 2 performs a rotational movement relative to the cap 2 via the thread 33a which engages with the attachment component 1. This relative rotational movement of the threaded insert 33 causes the sealing element 30, mounted on the cap 2 such that it can move about the element 2a, to be rotated via the edge 33b of the threaded insert 33 abutting one side on the sealing element 30, as will be explained in detail below by referring to FIGS. 14A to 14F, and the cannula passage opening 7 to be exposed.

Figure 13:
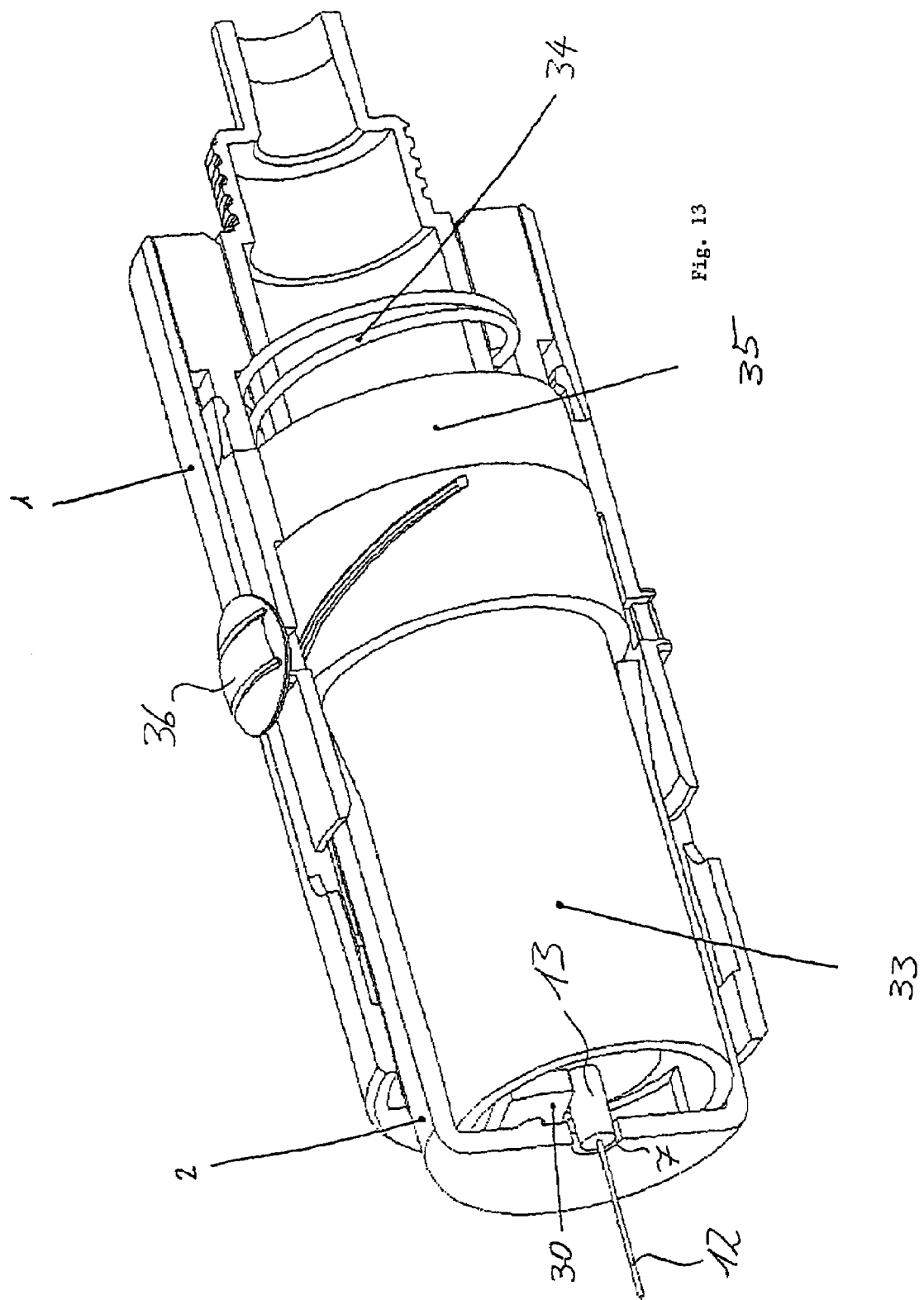
FIG. 13 depicts the cannula cover of FIG. 12, with the cannula exposed.

FIG. 13 shows the cannula passage opening 7 completely exposed, the sealing element 30 having completely exposed the cannula passage opening 7 and therefore enabled passage for the cannula 12 arranged on the cannula support 13.

In accordance with the fifth embodiment, the cap 2 is only unlatched by the user by operating the shifting element 36, and the cannula passage opening 7 and the cannula 12 can only be exposed when a pressure force is exerted on the front side of the cap 2. Erroneously exposing the cannula 12 is thus practically ruled out.

The sealing process occurs automatically once a pressure force is no longer acting on the cap 2, such that the spring 34 restores the threaded insert 33 and, therefore, the cap 2 back to the position shown in FIG. 11, wherein the locking projection 2a of the cap 2, biased outwardly, automatically locks in. For a further injection, it has to be exposed again by the user manually operating the shifting element 36. The cannula passage opening 7 can thus only be opened when the cap 2 is pressed onto an injection area, and is automatically sealed again.

Figure 14A:
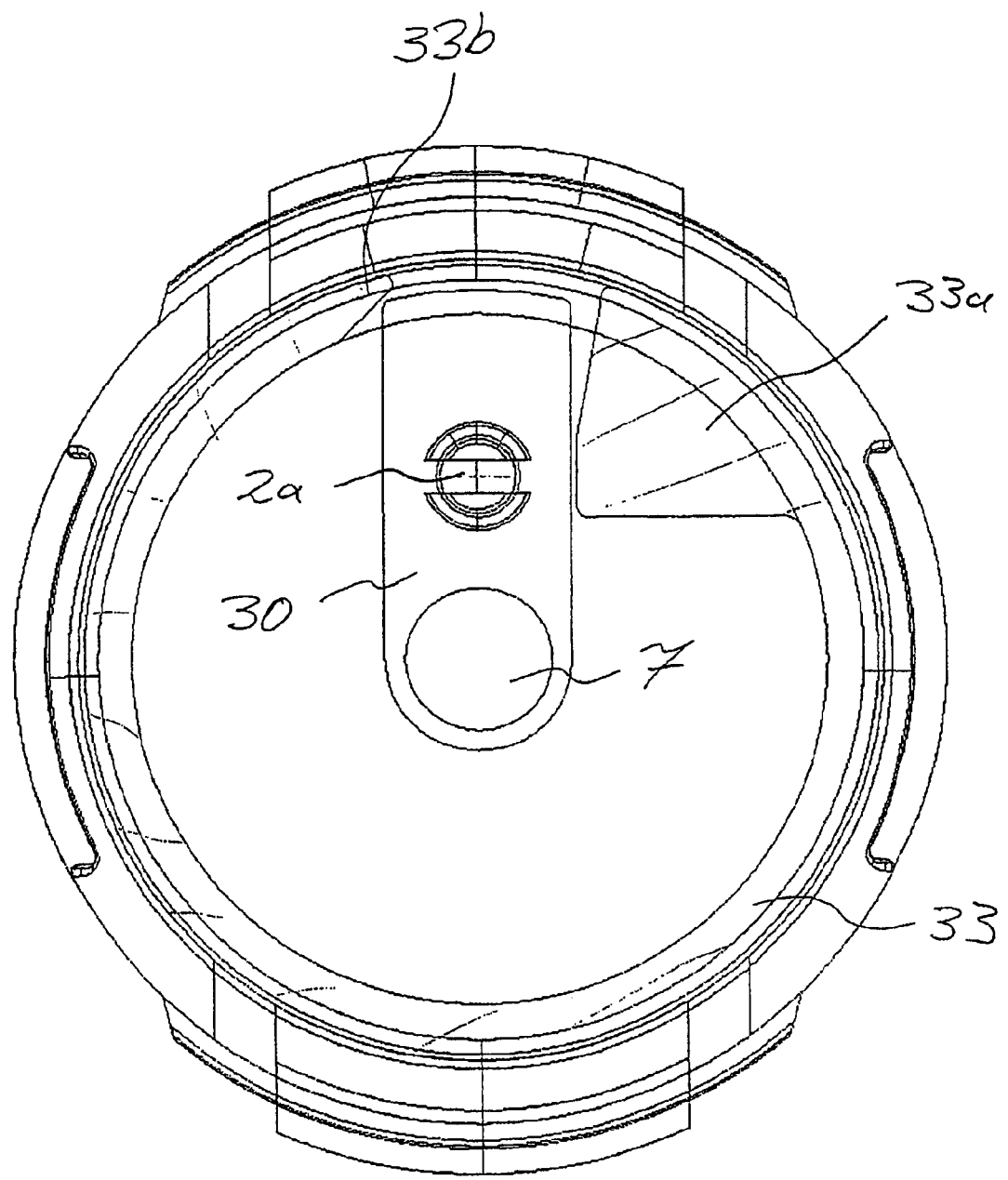
FIGS. 14A to 14F, is a top view onto the cannula cover shown in FIGS. 11 to 13, at various rotational angles of the threaded insert.

FIG. 14A shows a top view of the cannula cover shown in FIGS. 11 to 13, wherein the sealing element 30 lies in front of the cannula passage opening 7 and is mounted such that it can rotate about the element 2a. The lateral edges 33a and 33b of the threaded insert 33 do not abut the sealing element 30, such that the sealing element as shown in FIG. 11 exhibits a deflection of 0°.

Figure 14B:
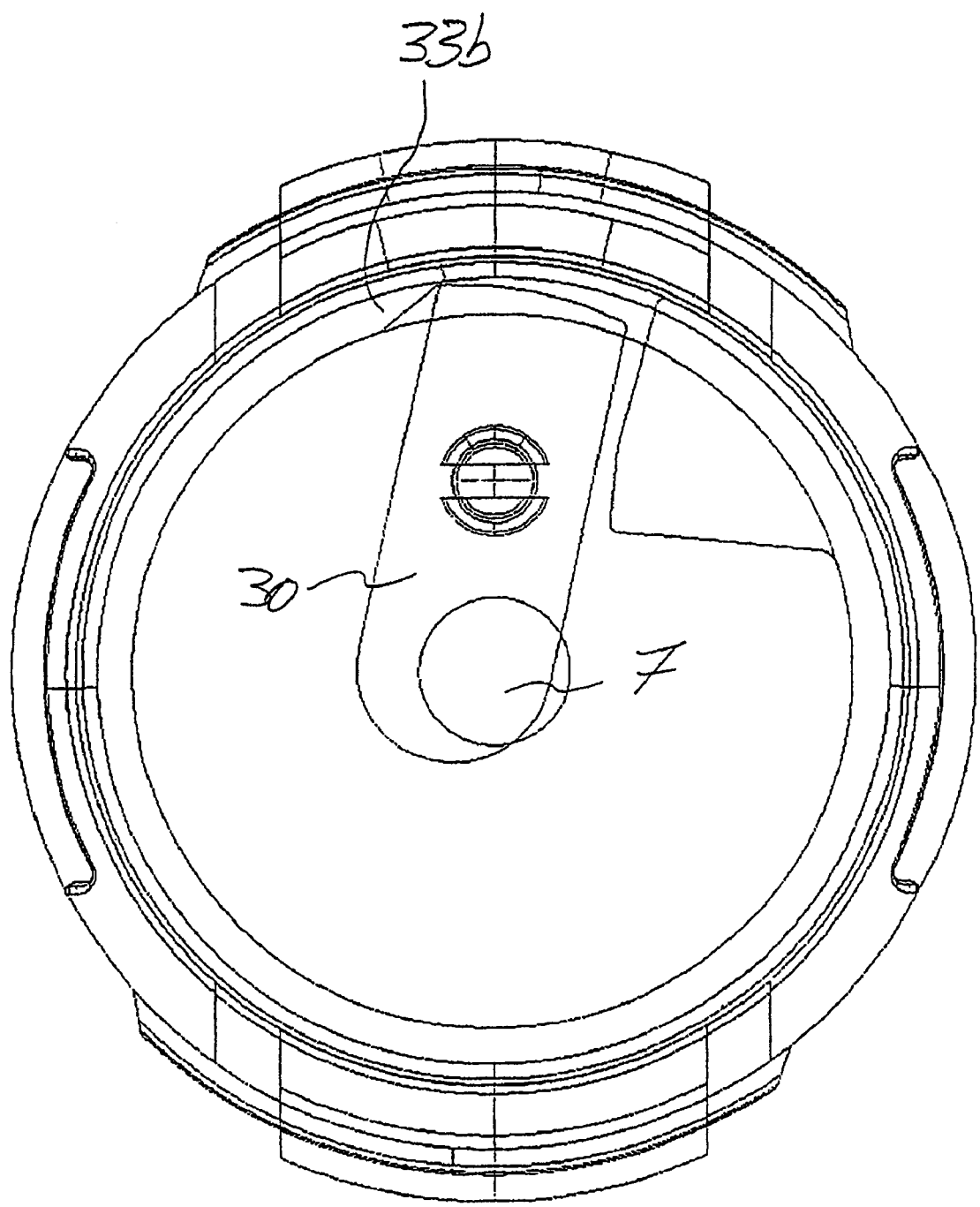

When a slight pressure is applied to the cap 2, the cap 2 is inserted slightly into the attachment component 1 and so causes a small initial rotational movement of the threaded insert 33, for example 5°, as shown in FIG. 14B, such that the sealing element 30 is slightly deflected laterally by the edge 33b of the threaded insert 33 abutting the sealing element 30.

Figure 14C:
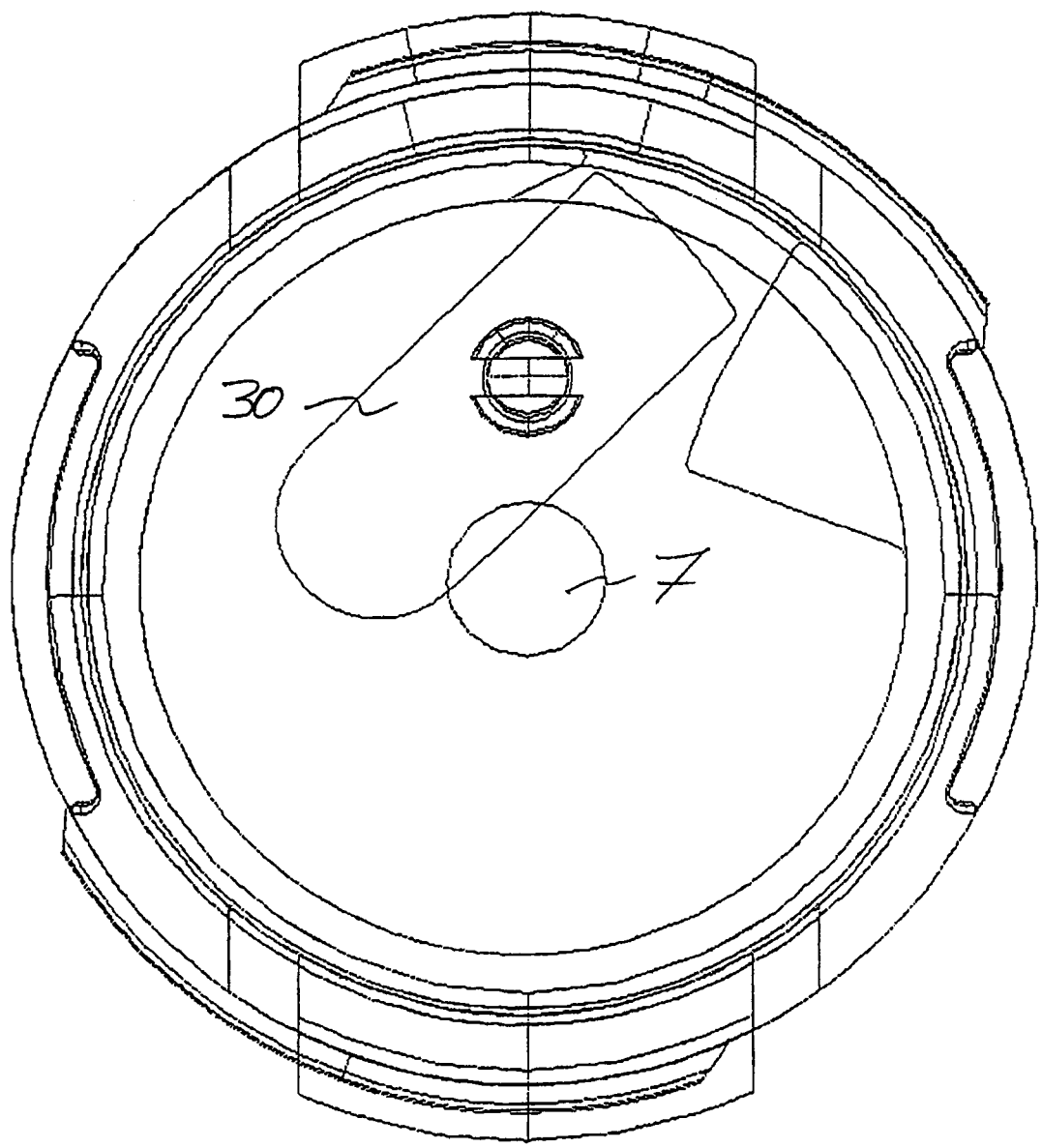
Figure 14D:
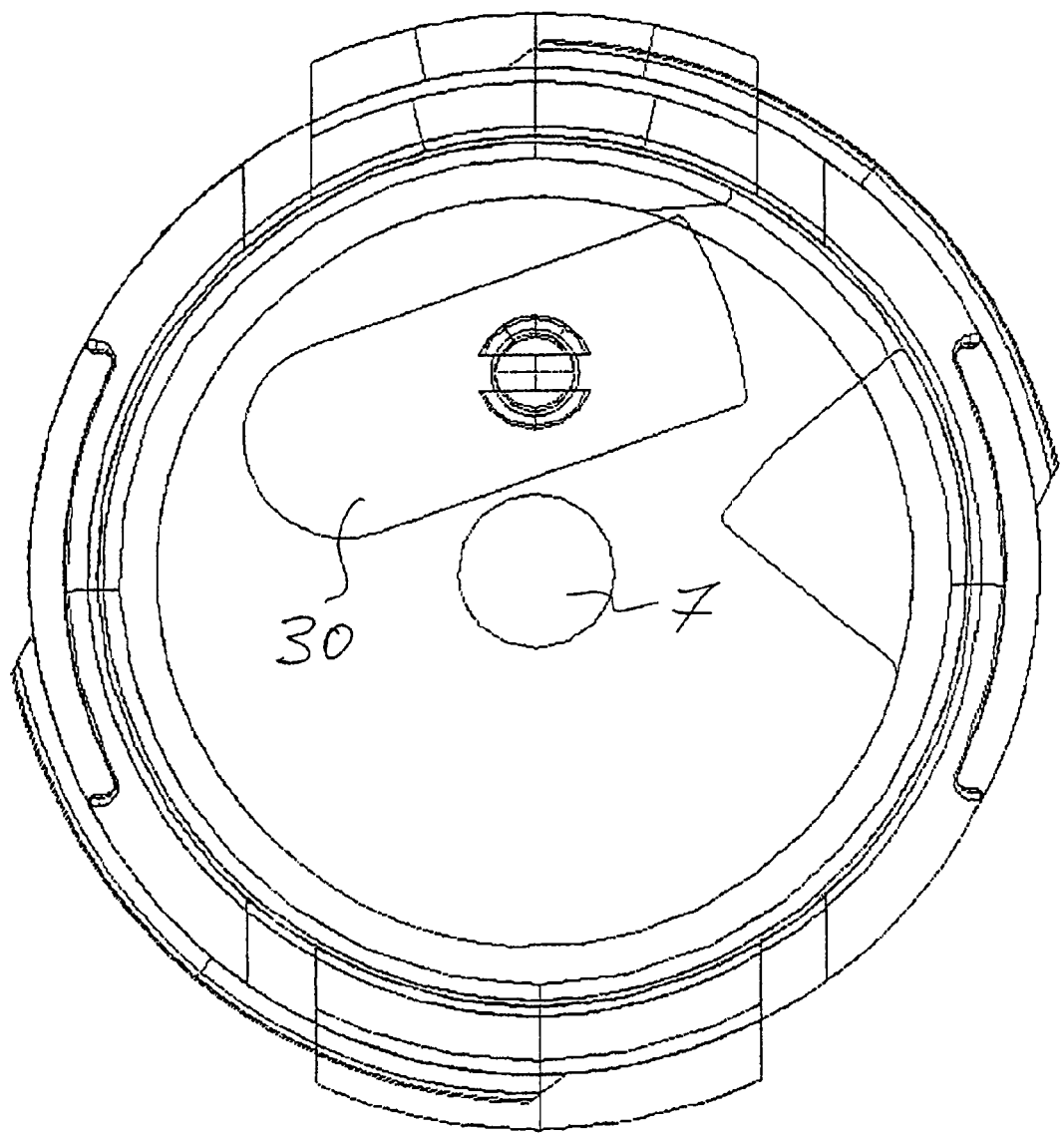

FIGS. 14C and 14D show rotations of the threaded insert 33 of 20° and 40° respectively, wherein the sealing element 30 is increasingly rotated and the passage opening 7 is eventually completely exposed, as shown in FIG. 14D.

Figure 14E:
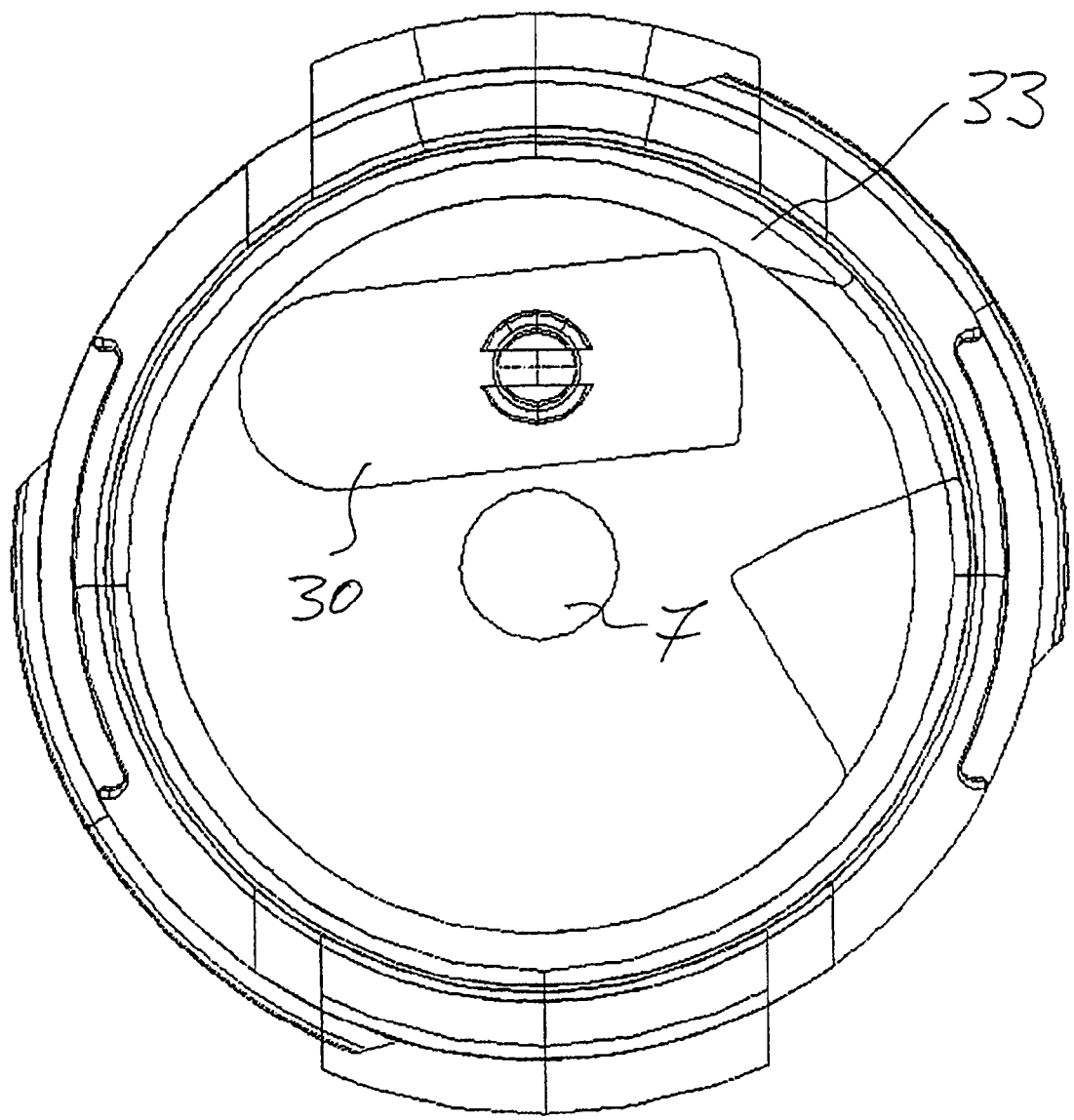

FIG. 14E shows a rotation of the threaded insert 33 of 60°, wherein the sealing element 30 has been deflected far enough and the threaded insert 33 has been rotated far enough that the sealing element 30 can no longer be returned to the resting position shown in FIG. 14A, since it is already abutting the threaded insert 33 with its right-hand upper edge. This prevents a rotational movement of the sealing element 30 back to seal the cannula passage opening 7.

Figure 14F:
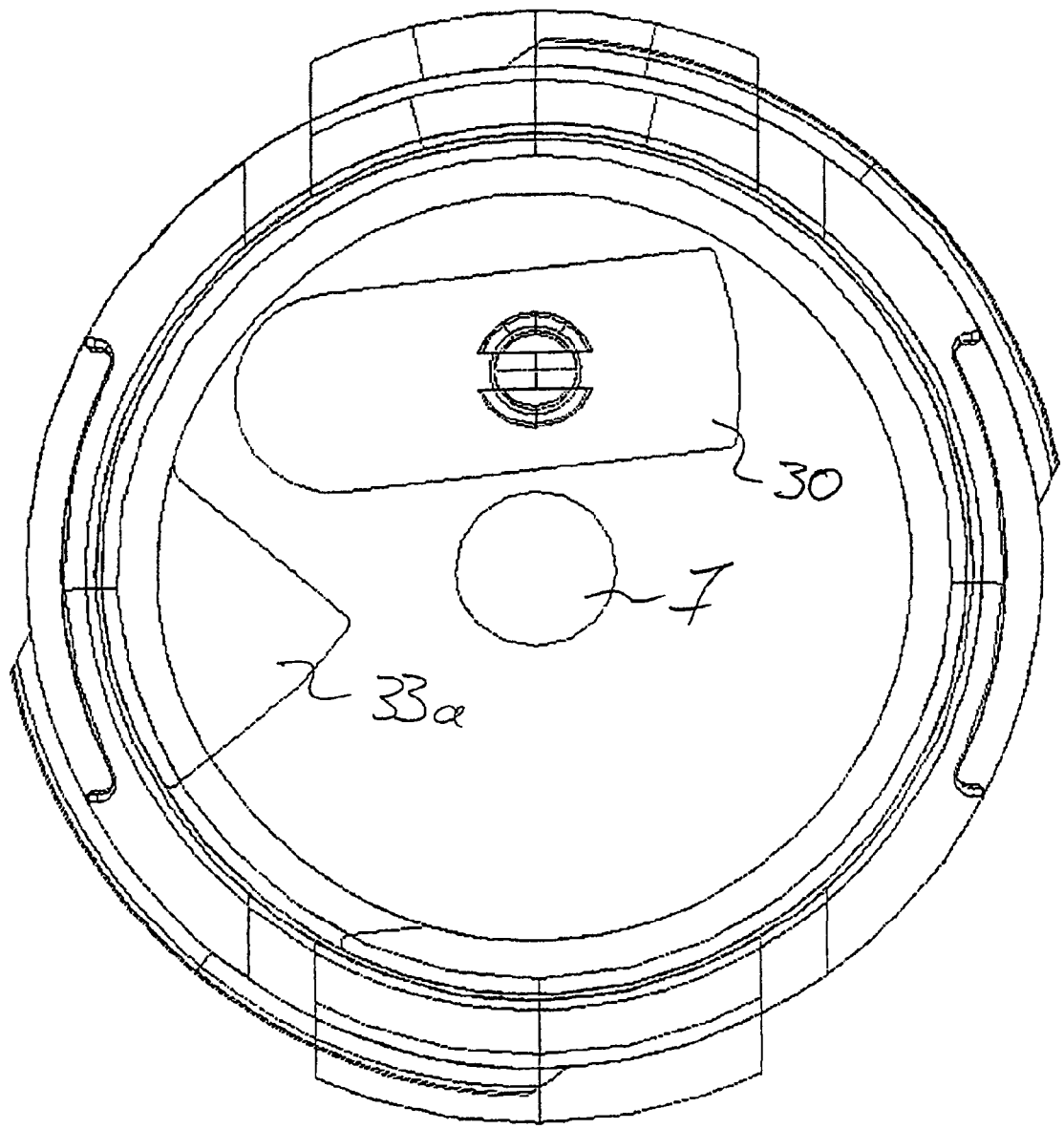

FIG. 14F shows the cannula passage opening 7 at a rotation of the threaded insert 33 of 220°, wherein the lateral edge 33a of the threaded insert 33 can additionally be used, when the threaded insert 33 is rotated further, to secure the rotated position of the covering element 30. This prevents the cannula passage opening 7 from being unintentionally closed by the covering element 30.

Common to all the embodiments is the fact that the front facing end of the cannula cover is substantially sealed and optimum protection for the cannula is thus ensured. The sealing mechanisms provide even better protection for the cannula against contamination and mechanical influences on the one hand, and on the other are each formed such that they are easy to handle in order to make it simple to administer the injection.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A cannula cover for an injector, comprising:
    a barrel-shaped cannula cap enclosing a cannula in an interior of the cap, the cap comprising a substantially closed end;
    a cannula passage opening formed at the substantially closed end; and
    a seal for the cannula passage opening, the seal comprising a slider and a latching strip, wherein in an initial position of the seal the cannula is blocked via the seal from exposure to the exterior of the cap, and in an exposing position of the seal the slider has been shifted on the body by a user sliding the slider along the cap, which retracts the latching strip from the cannula passage opening to expose the cannula to the cap exterior prior to the cannula emerging through the cannula passage opening, wherein when the seal is in the exposing position, said cover can be retracted to expose the cannula.

2. The cannula cover as set forth in claim 1, further comprising a latch which can be unlatched by rotating the cover, said latch preventing the cover from being retracted.

3. The cannula cover as set forth in claim 2, wherein the sealing strip can be shifted by shifting the slider in the circumferential direction on the cover, and wherein a movement direction component may be shifted.

4. The cannula cover as set forth in claim 3, wherein the slider simultaneously unlatches the latch preventing the cover from being retracted.

5. The cannula cover as set forth in claim 1, wherein said sealing strip can be shifted directly by longitudinally shifting said slider.

6. The cannula cover as set forth in claim 1, wherein the cover can only be retracted when a generally axial force acts on the cover on the front facing side.

7. The cannula cover as set forth in claim 6, wherein a spring is arranged in the cap and urges the cap to a forward position.

8. The cannula cover as set forth in claim 2, wherein the cover can only be retracted when the cover has been rotated and a generally axial force acts on the cover on the front facing side.

9. The cannula cover as set forth in claim 8, wherein a spring is arranged in the cap and urges the cap to a forward position.

10. The cannula cover as set forth in claim 1, wherein, in the initial position, the latching strip extends along a longitudinal length of the cap and at an angle along the substantially closed end of the cap.

11. The cannula cover as set forth in claim 1, further comprising a longitudinal guide arranged on the cap, the latching strip guided in the longitudinal guide from the initial position to the exposing position.

12. The cannula cover as set forth in claim 11, further comprising an attachment arranged over the latching strip such that the latching strip is slidably held between the guide and the attachment.

13. The cannula cover as set forth in claim 12, wherein the slider is further configured to slide laterally in the circumferential direction, and wherein the latching strip is guided between the attachment and the guide such that lateral movement of the slider in the circumferential direction generates a longitudinal movement of the latching strip up to the exposing position.

14. The cannula cover as set forth in claim 12, further comprising a latch preventing the cover from being retracted, and wherein the slider is configured to slide laterally in the circumferential direction to unlatch the cover.

15. The cannula cover for an injector, comprising:
    an attachment component configured to be coupled to the injector;
    a spring arranged around an exterior of the attachment component;
    a cap enclosing a cannula in a cap interior comprising:
        a substantially closed first end;
        a cannula passage opening formed in the substantially closed first end;
        a second end configured to receive the attachment component and the spring such that the spring biases the cap away from the attachment component; and
        at least two other passages arranged proximate the second end; and
    at least two sealing elements arranged in the interior of the cap and coupled to the exterior of the attachment component, each sealing element comprising:
        an elongated tongue extending along a longitudinal length of an interior of the cap and terminating proximate the first end;
        a sealing section formed on the tongue for sealing the cannula passage opening in an initial position of the cap; and a locking attachment in a base area of the sealing element, the locking attachment configured to form a locking arrangement with the one of the other cap passages;

wherein in the initial position of the cap, the sealing elements are arranged adjacent to each other and form a block between the cannula passage opening and the cannula arranged in the interior of the cap, and in a shifted position of the cap, the tongues are pushed apart, and in response, the sealing elements are moved away from the cannula passage opening such that the cannula can emerge through the opening.

16. The cannula cover as set forth in claim 15, wherein the attachment component further comprises openings configured to receive the tongues of the sealing components such that the tongues are arranged in an interior of the spring, and the sealing sections come together in front of the cannula passage opening to form the seal.

* * * * *